(12) United States Patent
Fesmire et al.

(10) Patent No.: US 6,487,866 B1
(45) Date of Patent: Dec. 3, 2002

(54) MULTIPURPOSE THERMAL INSULATION TEST APPARATUS

(75) Inventors: James E. Fesmire, Titusville, FL (US); Stanislaw D. Augustynowicz, Titusville, FL (US)

(73) Assignee: The United States of America as represented by the National Aeronautics & Space Administration, Washington, DC (US)

( * ) Notice: Subject to any disclaimer, the term of this patent is extended or adjusted under 35 U.S.C. 154(b) by 0 days.

(21) Appl. No.: 09/906,011

(22) Filed: Jul. 9, 2001

Related U.S. Application Data

(60) Provisional application No. 60/217,317, filed on Jul. 10, 2000.

(51) Int. Cl.[7] .......................... F25B 19/00; G01N 25/18
(52) U.S. Cl. .......................................... 62/51.1; 374/44
(58) Field of Search ............................ 62/51.1; 374/43, 374/44, 29

(56) References Cited

U.S. PATENT DOCUMENTS

| | | | |
|---|---|---|---|
| 3,948,409 A | | 4/1976 | Ovchinnikov et al. |
| 4,848,093 A | * | 7/1989 | Simmonds et al. .......... 62/49.1 |
| 4,848,103 A | | 7/1989 | Pelc et al. |
| 4,929,089 A | * | 5/1990 | Tsuchida ..................... 374/44 |
| 5,004,354 A | * | 4/1991 | Utten et al. ................... 374/29 |
| 5,258,929 A | * | 11/1993 | Tsuchida .................... 364/557 |
| 5,537,829 A | | 7/1996 | Jones et al. |
| 5,589,020 A | | 12/1996 | Varghese |
| 5,806,979 A | * | 9/1998 | Gschneider et al. .......... 374/34 |
| 5,974,784 A | | 11/1999 | Feldman |
| 5,988,875 A | * | 11/1999 | Gershfeld et al. ............ 374/10 |

OTHER PUBLICATIONS

Shoji Kamiya et al., "Basic Design of Large Apparatus for Measuring Insulator fS Thermal Conductivity", 1997.
Jon Wikstrom et al., "Study of Cryogenic Insulation Systems", 1998 "Cryostat Test Apparatus for Thermal Insultation System Development", Dec. 4, 1998.
American Society for Testing and Materials, "C745–92 (1999) Standard Test Method for Heat Flux Through Evacuated Insulations Using a Guarded Flat Plate Boiloff Calorimeter", 1999.
NASA Lewis Research Center, "Supplemental Multilayer Insulation Research Facility (SMIRF)".

* cited by examiner

*Primary Examiner*—William C. Doerrler
(74) *Attorney, Agent, or Firm*—Randall M. Heald; Gary G. Borda; John G. Mannix

(57) ABSTRACT

A multi-purpose thermal insulation test apparatus is used for testing insulation materials, or other components. The test apparatus is a fluid boil-off calorimeter system for calibrated measurement of the apparent thermal conductivity (k-value) of a specimen material at a fixed vacuum level. The apparatus includes an inner vessel for receiving a fluid with a normal boiling point below ambient temperature, such as liquid nitrogen, enclosed within a vacuum chamber. A cold mass assembly, including the inner vessel and thermal guards, is suspended from the top of the vacuum chamber. Handling tools attach to the cold mass assembly for convenient manipulation of the assembly and for the installation or wrapping of insulation test materials. Liquid nitrogen is typically supplied to the inner vessel using a fill tube with funnel. A single port through the top of the vacuum chamber facilitates both filling and venting. Aerogel composite stacks with reflective films are fastened to the top and the bottom of the inner vessel as thermal guards. The comparative k-value of the insulation material is determined by measuring the boil-off flow rate of gas, the temperature differential across the insulation thickness, and the dimensions (length and diameters) of the test specimen.

18 Claims, 7 Drawing Sheets

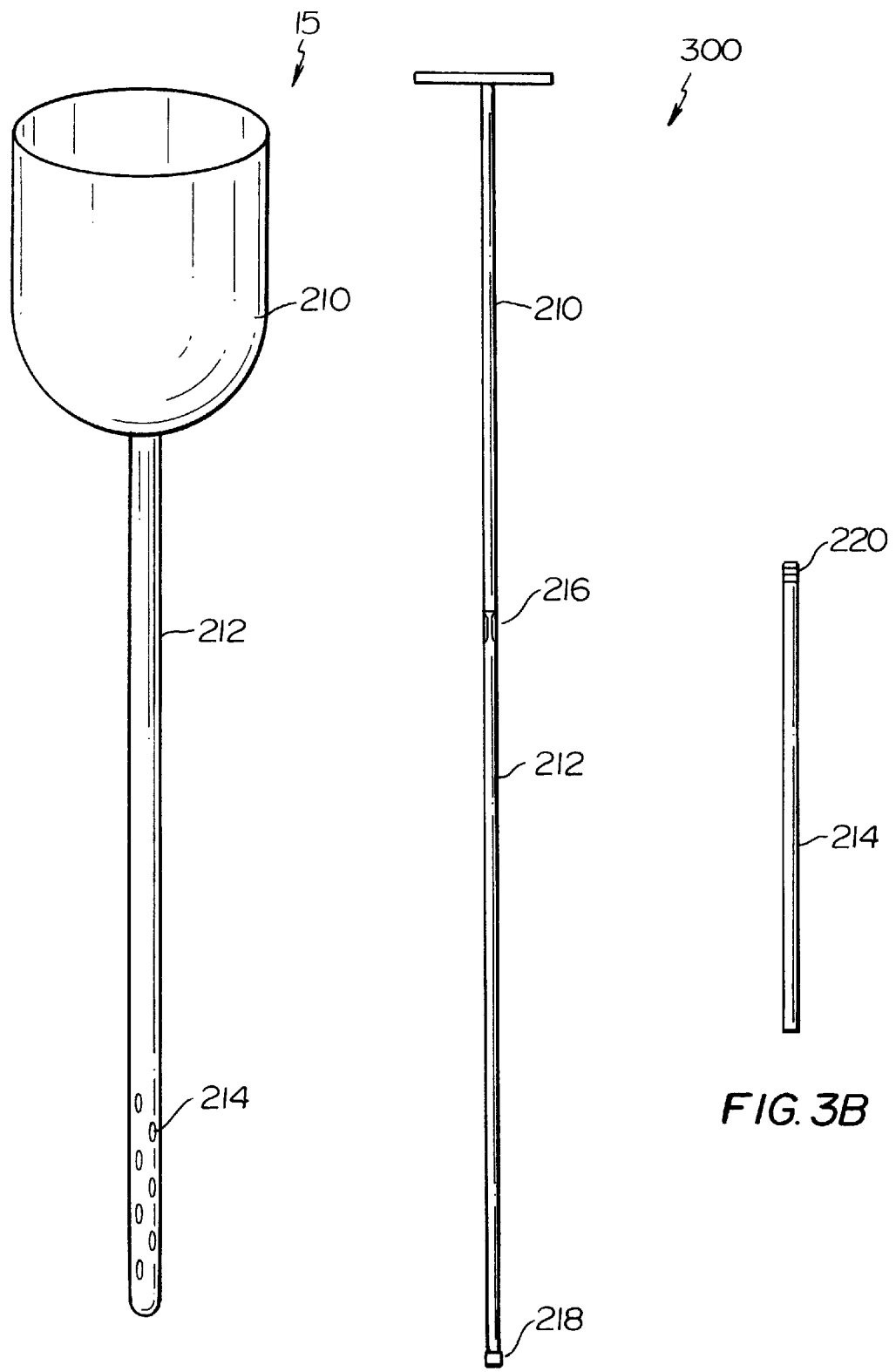

US 6,487,866 B1

MULTIPURPOSE THERMAL INSULATION TEST APPARATUS

PRIORITY CLAIM UNDER 35 U.S.C. 119(e)

This application claims the benefit, under 35 USC 119(e), of U.S. Provisional Application No. 60/217,317 filed Jul. 10, 2000, the contents of which are incorporated herein by reference.

ORIGIN OF THE INVENTION

The invention described herein was made in the performance of work under a NASA contract and by an employee of the United States Government and is subject to the provisions of Public Law 96-517 (35 U.S.C. 202) and may be manufactured and used by or for the Government for governmental purposes without the payment of any royalties thereon or therefore. In accordance with 35 U.S.C. 202, the contractor elected not to retain title.

BACKGROUND OF THE INVENTION

This invention relates to the field of cryogenic testing of material to determine the thermal performance of a material or system of materials.

One valuable technique for testing the thermal performance of materials, preferably insulation material, is boil-off testing. Boil-off testing is accomplished by filling a vessel with a fluid which boils below ambient temperature. Although the preferred fluid is the cryogen liquid nitrogen, other fluids such as liquid helium, liquid methane, liquid hydrogen, or known refrigerants may be used. Once the vessel is filled with the cryogenic fluid, the vessel is surrounded with the testing material. A calorimetry method is then used to determine the thermal conductivity of the testing material by first determining the amount of heat that passes through the test material to the vessel containing cryogenic fluid. The cryogenic fluid boil-off rate from the vessel is directly proportional to the heat leak rate passing through the test material to the cryogenic fluid in the vessel. For a test material under a set vacuum pressure, the apparent thermal conductivity (k-value) is determined by measuring the flow rate of cryogenic boil-off at given warm and cold boundary temperatures across the thickness of the sample.

Although cryogenic boil-off techniques and devices have been prepared to determine the thermal conductivity of insulation material, the previous techniques and devices are undesirable for a variety of reasons. First, few such cryogenic devices are in operation because of their impracticality from an engineering point of view. The previous cryogenic boil-off devices made it extremely difficult to obtain accurate, stable measurements and required extremely long set up times. Prior testing devices also needed highly skilled personnel that could oversee the operation of the cryogen testing device for extended periods of time, over 24 hours to many days in some cases. Additionally, constant attention was required to operate previous cryogenic testing devices to make the necessary fine adjustments required of the testing apparatus. Second, prior cryogenic testing devices contained the limitation that they did not permit the testing of continuously rolled products which are commonly used insulation materials. The testing of high performance materials such as multilayer insulation requires extreme care in fabrication and installation. Inconsistency in wrapping techniques is a dominant source of error and poses a basic problem in the comparison of such materials. Improper treatment of the ends or seams can render a measurement several times worse than predicted. Localized compression effects, sensor installation, and outgassing are further complications. Third, measurements of various testing parameters were not carefully determined or controlled in previous testing devices. Measurement of temperature profiles for insulation material was either not done or was minimal because of the practical difficulties associated with the placement, feed-through, and calibration of the temperature sensors. Vacuum levels were restricted to one or two set points or not actively controlled altogether. Fourth, previous cryogenic testing devices required complex thermal guards having cryogenic fluid filled chambers to reduce unwanted heat leaks (end effects) to a tolerable level. The previous technique for providing thermal guards, filling guard chambers with the cryogen, caused much complexity both in construction and operation of the apparatus. Known techniques add the further complication of heat transfer between the test chamber and the guard chambers due to thermal stratification of the liquid within the chambers

SUMMARY OF THE INVENTION

To eliminate or minimize the foregoing and other problems, a new method of fabricating and testing cryogen insulation systems has been developed. In particular, the present invention ad overcomes the foregoing problems by providing a cryogenic testing apparatus having a boil-off calorimeter system for calibrated measurement of the apparent thermal conductivity (k-value) of a testing material, preferably insulation material, at a fixed vacuum level. The cryogenic testing apparatus includes a vacuum chamber that contains an inner vessel that receives cryogenic fluid, for example liquid nitrogen, helium, hydrogen, methane or other known refrigerants. The apparatus incorporates a number of design features that minimize heat leak, except through specific portions of the inner vessel. For example, the top and the bottom of the inner vessel are abutted with thermal guards, such as silica aerogel composite plugs, to ensure thermal stability of the cryogenic environment. The inner vessel with the thermal guards is called a cold mass assembly upon which the test specimen is installed. The heat leak rate through the top and bottom of the inner vessel is reduced to a fraction of the heat leak through the sidewalls of the vessel. Temperature sensors are placed between layers of the testing material that is wrapped around the cold mass assembly to obtain temperature-thickness profiles. The apparent thermal conductivity (k-value) of the testing material is determined by measuring the boil-off flow rate of the cryogenic fluid and temperature differential between a cold boundary temperature and a warm boundary temperature for a known thickness of the testing material.

During the preferred use, the cold mass assembly is easily and quickly removed from the vacuum chamber and placed on an insulation-wrapping machine preferably using special handling tools. Temperature sensors, preferably thermocouples, are placed at various thicknesses within the testing material. A first temperature sensor on the inner vessel is designated the cold boundary temperature sensor. The cold boundary temperature may also be determined from the known boil-off temperature of the cryogenic fluid. A second temperature sensor on the outer surface of the testing material is designated the warm boundary temperature ID sensor. The warm boundary temperature sensor may be placed at any known distance from the inner vessel. After the testing material is secured to the cold mass assembly, the cold mass assembly is installed within the vacuum chamber using a special handling tool such that the insulation test specimen remains undisturbed and untouched. Preferably, the cold mass assembly is suspended by a plurality of support threads, such as three KEVLAR threads with hooks and hardware for attachment and length adjustment. KEVLAR threads have a low thermal conductivity, a high tensile strength and greatly resist elongation. Therefore, a relatively small diameter KEVLAR thread is preferred to minimize any additional heat transfer to the inner vessel. Once the cold mass assembly is secure, the handling tool is removed, and the vacuum chamber is sealed, the cryogenic fluid is supplied to the inner vessel, preferably using a specially designed funnel and fill tube, until the inner vessel is full and at a constant temperature. The vacuum chamber is maintained at a constant vacuum, using a preferred vacuum pumping and gas metering system, and a set sidewall temperature, using a preferred electrical heater system. The temperature differential between the cold boundary temperature and the warm boundary temperature of the testing material is measured by the temperature sensors and these values, along with the boil-off flow rate and the material thickness, are used to compute the comparative k-value. Calibration of the device, that is, determination of the total parasitic heat leak rate or "end effects", is accomplished by testing a material with a known k-value under the pressure and temperature conditions of interest. The actual k-value will therefore by slightly lower than the comparative k-value.

The present invention will overcome many shortcomings of the previous cryogenic boil-off devices. First, the testing device is more practical from an engineering viewpoint as compared with the previous devices. The present device can be employed in an automatic operation that requires little oversight by the operator. The design of the preferred silica aerogel i stacks as thermal guards is high performance and robust so that heat leak performance does not drift over time, thus resulting in a system calibration having long-term reliability and repeatability. The unique funnel and fill tube design allows for a one step cooling, filling and thermal stabilization process and eliminates the need for separate fill and vent ports in the inner vessel. This single port for filling and venting is constructed, in part, from thin wall stainless steel bellows which greatly increase the length of the path for conduction of heat from the vacuum chamber to the inner vessel. The parasitic heat leak to the inner vessel is therefore reduced to a minimum. Second, the present invention allows for the testing of large size prototype material systems in typical actual-use configurations. Of critical importance to the present invention is the ability to test continuously rolled insulation materials. This is highly desirable because other forms of insulation material, such as seamed blankets, can drastically affect the test results producing inaccurate readings in many cases. Although testing of continuously rolled insulation material is the preferred material to be tested by this device, a variety of other materials, other forms of material, or other components, may also be tested using the device. For example, bulk fill materials are tested using a containment sleeve with low thermal conductivity supports at the top and bottom. Other materials, including rigid or flexible types and clam-shell or blanket forms, are tested by afflixing the test specimen to the outside circumference of the cold mass assembly using tapes, wires, or other suitable means of attachment. Additionally, the ability to quickly change out the test article with another material is accomplished by the present invention. Third, a means for measuring the temperature profile across a known thickness of the insulation material is accomplished in order to characterize and understand the performance of the insulation system. Full range vacuum levels, varying from high vacuum to soft vacuum to atmospheric pressure, to higher pressures can be tested with a single device. Different residual gases such as air, nitrogen, helium, or carbon dioxide can be supplied to the vacuum chamber. The vacuum level can be maintained at a very steady value for long periods of time with accurate vacuum control and measurement. Fourth, the use of the preferred custom designed silica aerogel composite stacks for thermal guards eliminates the need for guard chambers containing cryogenic fluid. This feature also eliminates the problem of the effect of thermal stratification of the liquid inside the test chamber.

BRIEF DESCRIPTION OF THE DRAWINGS

The features and advantages of the present invention will become apparent from the following detailed description of a preferred embodiment thereof, taken in conjunction with the accompanying drawings, in which:

FIG. 2 depicts a funnel and fill tube assembly for cooling and filling the cold mass assembly in the device of FIG. 1;

FIG. 3 depicts handling tools for removal of the cold mass assembly from the vacuum chamber and wrapping of the cold mass assembly with a testing material;

DETAILED DESCRIPTION OF THE PREFERRED EMBODIMENT

Figure 1:
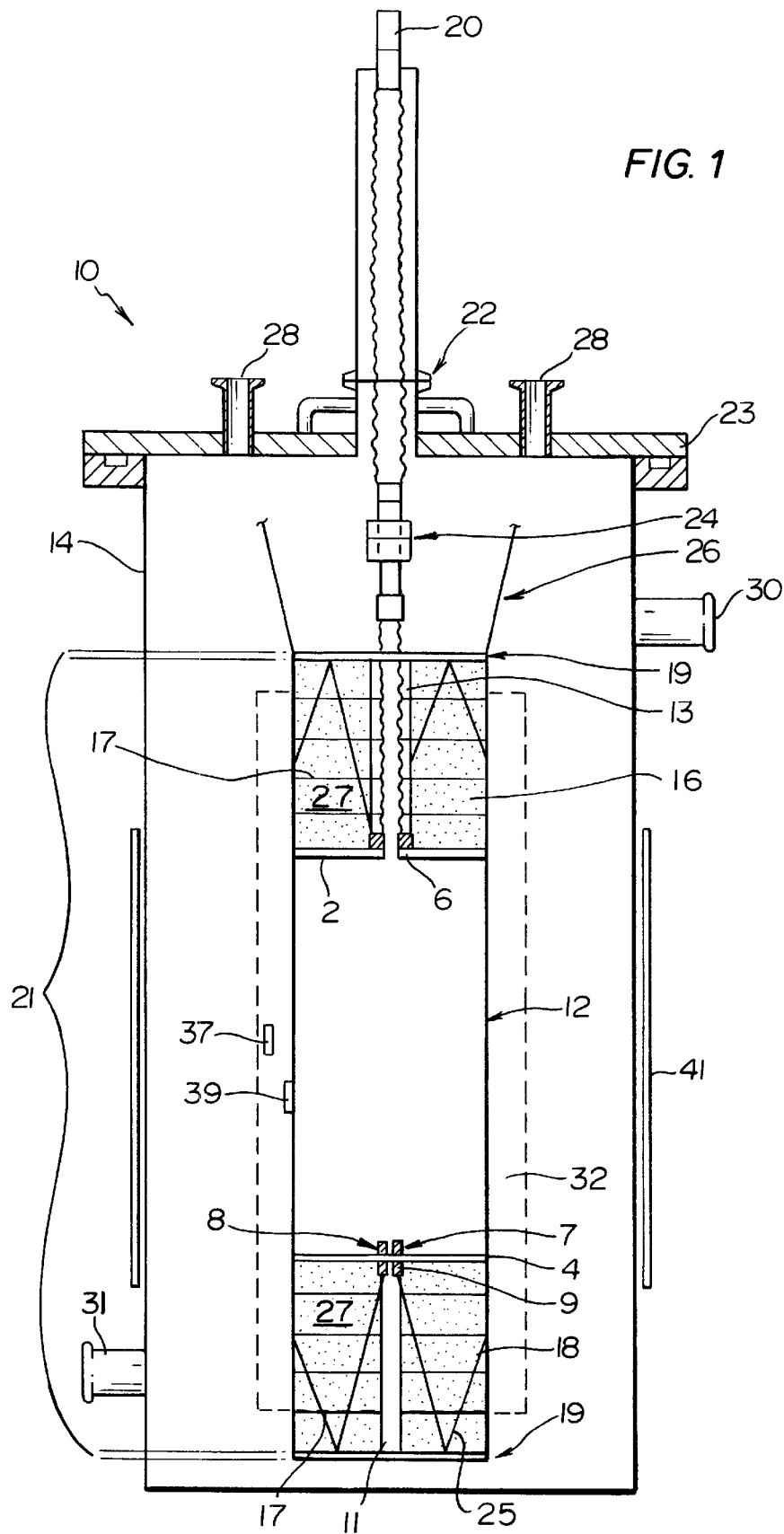
FIG. 1 is a side view of the cryogenic boil-off device that is constructed in accordance with the preferred embodiment of the invention.

Turning now to a detailed consideration of a preferred embodiment of the present invention, FIG. 1 shows a cryogenic boil-off device 10 with an inner vessel 12 enclosed within a vacuum chamber 14. The inner vessel 12 is made from any suitable material but is preferably a stainless steel cylinder having a top 2 and a bottom 4. The inner vessel 12 preferably has a socket weld 6 in the top 2 for securing the lower half of a cryogenic feed tube 20 to the inner vessel 12. A double ended connector 8 having a first connection 7 within the inner vessel 12 and a second connection 9 external to the inner vessel 12 is preferably welded into the bottom 4 of the inner vessel 12. Although the exact dimensions of the inner vessel are not critical, the surface area of the side of the inner vessel 12 is substantially larger, i.e., at least four times greater, than the surface area of the ends.

The inner vessel 12 is positioned between two thermal guards, a top thermal guard 16 and a bottom thermal guard 18. The top thermal guard 16 and bottom thermal guard 18 are each preferably a stack of silica aerogel composite discs 27 with a highly reflective film layer 17, such as silverlux reflective films or double-aluminized mylar films, between each disc 27. The preferred aerogel composite material is a nanoporous, extremely high surface area silica product reinforced by fiberglass, similar to the material by Aspen Systems, Inc in Marlborough, Mass. The top thermal guard 16 and bottom thermal guard 18 may be made from any suitable minsulation material as an alternative to the preferred silica aerogel composite material, such as balsa wood, cork, polyurethane foam, polystyrene foam and other insulating foams or materials. In a prototype of the invention, the discs 27 were approximately 5 inches in diameter and 1 inch in thickness. A total of five discs were used per stack for a thermal guard 5 inches in length. The stacks are held together by lacings of thread 25, preferably KEVLAR, between end caps 19 and the inner vessel 12. Also, one wrap of reflective film or foil goes around the circumference of each thermal guard stack of discs 27. However, the dimensions of the discs 27 may vary depending of the size of the inner vessel 12 and the amount of insulation needed to reduce the unwanted heat loss. The top thermal guard 16 has a hole 13 to allow for the passage of the cryogenic feed tube 20. The bottom thermal guard 18 also has a hole 11 to allow for the passage of a bottom handling tool 214, as discussed below. The hole 11 in the bottom thermal guard may be filled with insulating material during testing to minimize heat leak through the hole 11. The top thermal guard 16 and the bottom thermal guard 18 are secured by preferably glass-fabric-reinforced epoxy composite G-10 end caps 19 which are laced to the inner vessel 12 using fine lacings of thread 25, preferably aromatic polyamide fiber threads known as KEVLAR. The top thermal guard 16, bottom thermal guard 18, composite end caps 19 and inner vessel 12 are attached to form a cold mass assembly 21.

The cryogenic fluid, preferably liquid nitrogen, is delivered to the inner vessel 12 through the cryogenic feed tube 20. Any fluid, cryogenic or non-cryogenic, that boils below ambient conditions may be used, for example liquid helium, liquid hydrogen, liquid nitrogen, liquid oxygen, liquid methane, and other refrigerants. The cryogenic feed tube 20 passes through a feedthrough port 22 in a top of the vacuum chamber 23, preferably a flange, through the hole 13 in the top thermal guard 16, and is fitted onto the socket weld 6 at the top 2 of the inner vessel 12. The cryogenic feed tube 20 is preferably constructed from thin-wall tubing and thin-wall bellows and contains a type VCR coupling 24 which allows for cryogenic fluid filling, venting and boil-off Although the cryogenic feed tube 20 may be any suitable dimension, in a prototype of the invention the cryogenic feed tube 20 was approximately ½ inch in diameter and approximately 19 inches long. The bellows portion of this overall length is maximized in order to minimize the heat leak to the inner vessel. A funnel and fill tube 15, as shown in FIG. 2, is preferably employed to deliver the liquid to the inner vessel 12, and allows for the cooling and filling of the inner vessel 12 with the given cryogenic fluid. The funnel 15 has a large fluid receiving portion 210 connected to tubing 212 that extends through the cryogen feed tube 20 to the bottom of the inner vessel 12. A series of small holes 214 in the wall of the lower portion of the tubing 212 allows for the inner vessel 12 to be fed with liquid cryogen. The tubing 212 is sized smaller than the inside diameter of the feed tube 20 such that the vent gas may exit the inner vessel 12 during the filling process. The cryogenic feed tube 20 and funnel and fill tube 15 permit the combined filling and venting of the inner vessel 12 so that additional ports in the inner vessel are unnecessary. Any additional ports would increase the unwanted heat leak from the inner vessel 12 and introduce additional complications during installation and removal of the cold mass assembly 21.

The entire cold mass assembly 21, including the inner vessel 12, top thermal guard 16 and bottom thermal guard 18, is disposed within the vacuum chamber 14. Preferably, the inner vessel 12 is suspended by a plurality of threads 26, preferably aromatic polyamide fiber threads known as KEVLAR, attached to adjustable eye-hooks in the flange 23 of the vacuum chamber 14. The vacuum chamber 14 also contains temperature sensor feed through ports 28, a vacuum measuring port 30, and a vacuum pump port 31 for regulating and controlling the temperature and pressure of the vacuum chamber 14. It is important to clarify that all the preferred dimensions listed are designed to first and foremost reduce the heat leak to the inner vessel 12, also known as "parasitic" heat, to as small as possible for the full range of vacuum. Although the dimensions listed above disclose one preferred embodiment, a variety of dimensions may be suitable for the present invention as long as the "parasitic" heat leak remains small. The dimensional features described are also intended to take into account the handling, installation, and safety features.

To facilitate testing of a testing material 32 using the cryogenic boil-off device 10, the cold mass assembly 21 may be removed from the vacuum chamber 14 and installed on an insulation-wrapping machine, e.g. an 18-inch wide wrapping machine, preferably using a specialized tool 300 as depicted in FIG. 3. But first, the top 23 of the vacuum chamber with the cold mass assembly 21 attached is lifted and put on an open work stand. The specialized tool 300 has a T-handled portion 210, a top handling tool 212, and a bottom handling tool 214. The T-handled portion 210 attaches to the top handling tool 212 at a threaded screw connection 216. The top handling tool 212 also has an inner vessel attachment 218 so that the top handling tool 212 may be attached to the bottom 4 of the inner vessel 12 at the first connection 7 of the double ended connector 8. The top handling tool 212 is afixed to the bottom 4 of the inner vessel 12 by passing the top handling tool 212 through the lower half of the cryogen feed tube 20 and through the inner vessel 12 until the top handling tool 212 abuts the bottom 4 of the inner vessel 12 where the inner vessel attachment 218 attaches to the first connection 7 of the double ended connector 8. The bottom handling tool 214 has an outer attachment 220 for connecting with the inner vessel 12. The bottom handling tool 214 is placed through hole 11 in the bottom thermal guard 18 until it abuts the bottom 4 of the inner vessel 12. The outer attachment 220 attaches to the second connection 9 of the double ended connector 8. Once the top handling tool 212 and the bottom handling tool 214 are attached to the inner vessel, the cold mass assembly 21 may be lowered using the T-handled portion 210 until the bottom handling tool 214 contacts the lower surface of the work stand. The suspension threads 26 are unhooked, the VCR fitting 24 is disconnected, and then the T-handled portion 210 can be disconnected from the top handling tool 212. The cold mass assembly 21 can then be conveniently handled and placed on the wrapping machine using the top handling tool 212 and the bottom handling tool 214.

A plurality of temperature sensors 37, 39 are positioned at various known thicknesses with in the testing material 32. At least one temperature sensor 39 is positioned on the inner vessel 12 to measure the cold boundary temperature. However, the inner temperature sensor 39 may be optional since the inner temperature should closely approximate to the known boiling point of the cryogen. At least one temperature sensor 37 is positioned on the outer surface of the testing material 32 to measure the warm boundary temperature. Any known temperature sensor 37, 39, for example thermocouples, may be used to measure the temperature at the various thickness of the testing material 32. Additional temperature sensors may be placed at various thicknesses in the testing material 32. After the testing material 32 is secured to the cold mass assembly 21 and the temperature sensors 37, 39 are in place, the specialized tool 300 and the cold mass assembly 21 are suspended from the top 23 of the vacuum chamber, preferably by threads 26 such as aromatic polyamide fiber threads known as KEVLAR. Since KEVLAR has a high tensile strength and a strong resistance to elongation, a relatively small diameter thread may be used to support the inner vessel 12 resulting in less heat loss through the thread 26. The T-handled portion 210 is slid through the cryogenic feed tube 20 and connected to the top handling tool 212. Once the cold mass assembly 21 is raised up by using the T-handled portion 210 and the VCR fitting 24 is tightened, it is then secured by preferably three threads 26 having length adjustment hardware. The bottom handling tool 214 and the top handling tool 212 with the T-handled portion 210 are removed. Bottom hole 11 is plugged with insulation material, such as fiberglass, and the temperature sensor wires are connected to feed through 28. The top 23 of the vacuum chamber with the cold mass assembly 21 attached and testing specimen 32 installed is then lifted from the work stand and lowered into the vacuum chamber 14. Evacuation and heating of the vacuum chamber 14 are performed as required. Cryogenic fluid is supplied to the inner vessel 12 through the cryogenic feed tube 20 preferably using the funnel 15. The vacuum chamber 14 is then stabilized to maintain a constant vacuum and temperature, preferably using a blanket heater 41 that is controlled or set to certain warm temperatures. The temperature at the warm boundary layer and the cold boundary layer are measured by the temperature sensors 37, 39 and these values are used to compute the comparative k-value. As stated earlier, the cold boundary temperature may be determined from the known cryogenic fluid boiling point temperature based on the ambient pressure. The comparative apparent thermal conductivity (k-value) is determined by using the Fourier heat conduction equation:

$$\text{Heat Transfer Rate} = \frac{k(\text{Area})(\Delta T)}{\Delta x}$$

where, k=apparent thermal conductivity (k-value)

ΔT=temperature difference between the warm boundary surface and the cold boundary surface Δx=thickness of the testing material=$(d_o-d_i)/2$ The equation is modified for use of the cylindrical vessel to:

$$Q = \frac{2\pi k l (\Delta T)}{\ln\left(\frac{d_0}{d_i}\right)}$$

where:

l=effective length of the cold mass inner vessel $d_o$=outer diameter of insulation (warm boundary)

$d_i$=inner diameter of insulation (cold boundary)

Q=(Mdot)×($H_{fg}$)

$H_{fg}$=Heat of vaporization of the cryogen

Mdot=Mass flow rate of the boil-off gas

The mass flow rate (or boil off flow rate) is measured, typically, by two ways: flow meter and weight scale. The entire apparatus 10 is typically placed on a weight scale. Flow from one is simply used to check the flow from the other.

The surface area for a typical 1-inch thick insulation test article is 407 in². The measurable heat gain of the preferred embodiment of the invention is estimated to be from 0.100 to 40 watts corresponding to a nitrogen boil-off flow rate of 25 to 9,666 standard cubic centimeters per minute. The preferred operating temperature range is 77 to 373 K while the preferred operating pressure range is $1\times10^{-6}$ torr to 1,000 torr. Test article installation, evacuation and heating of the vacuum chamber 14, filling the inner vessel 12 with the cryogenic liquid, stabilization, and boil-offtest can be accomplished in a single day. The top and bottom thermal guards 16, 18 preferably made from silica aerogel composite stacks provide efficient thermal guarding (approximately 10% maximum of the total system heat leak depending on test specimen thickness and vacuum level test conditions). The test results obtained from this cryogenic boil-off device 10 have long-term repeatability and reliability.

Figure 4:
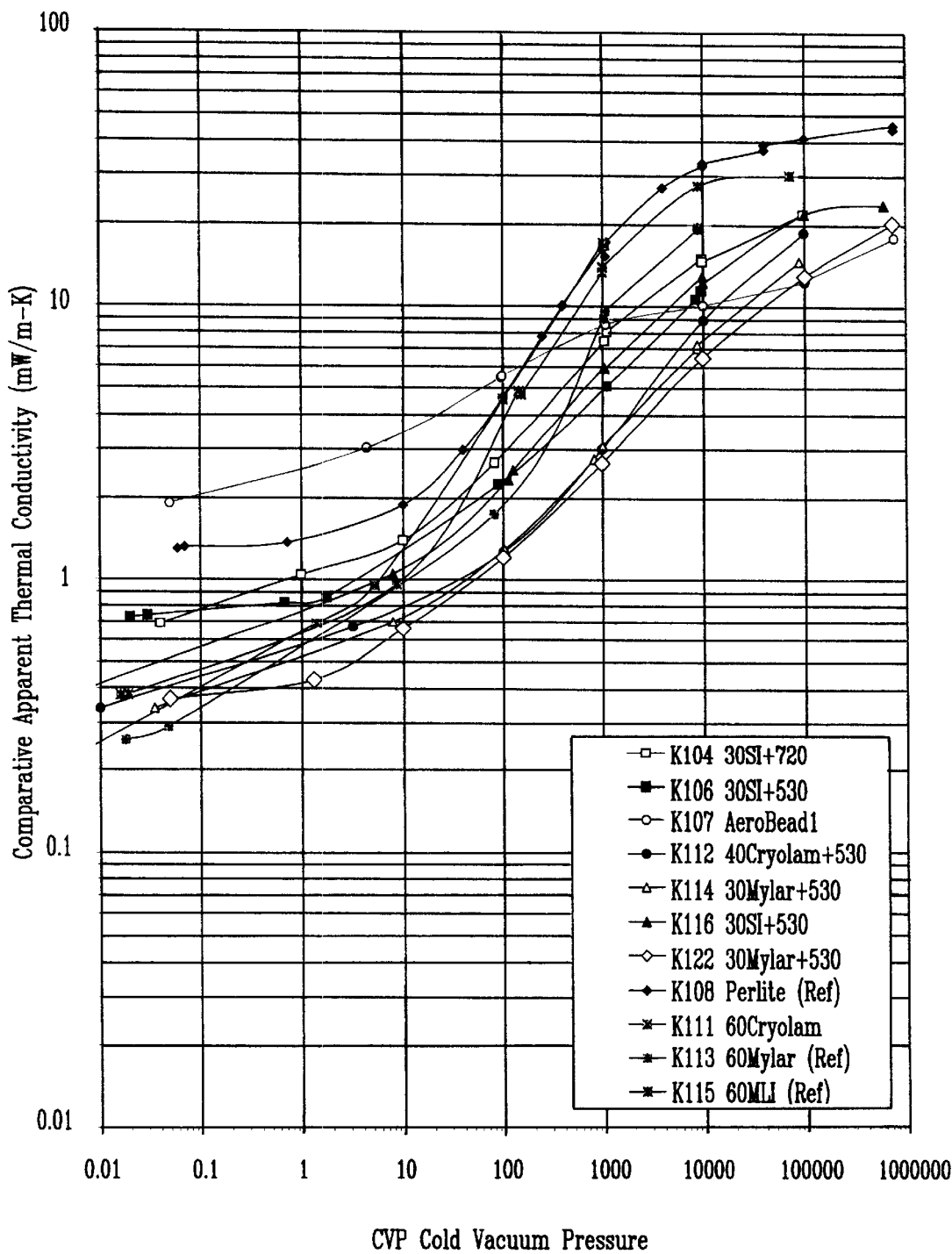
FIG. 4 is a graph showing the comparative k-values in milliwatts per meter-Kelvin as a function of cold vacuum pressure in microns (millitorr) for various testing materials over a wide range of vacuum levels.

FIG. 4 shows the comparative k-values in milliwatt per meter-Kelvin as a function of cold vacuum pressure in microns (or millitorr) for a variety of testing materials. The various materials that have been tested are shown in the legend in the lower right hand corner of the graph. This graph shows that the cryogenic boil-off device 10 can be used over a wide range of pressures from high vacuum to soft vacuum to no vacuum (ambient pressure). Previous cryogenic devices were specific to a set pressure region, either high vacuum or low vacuum.

Figure 5:
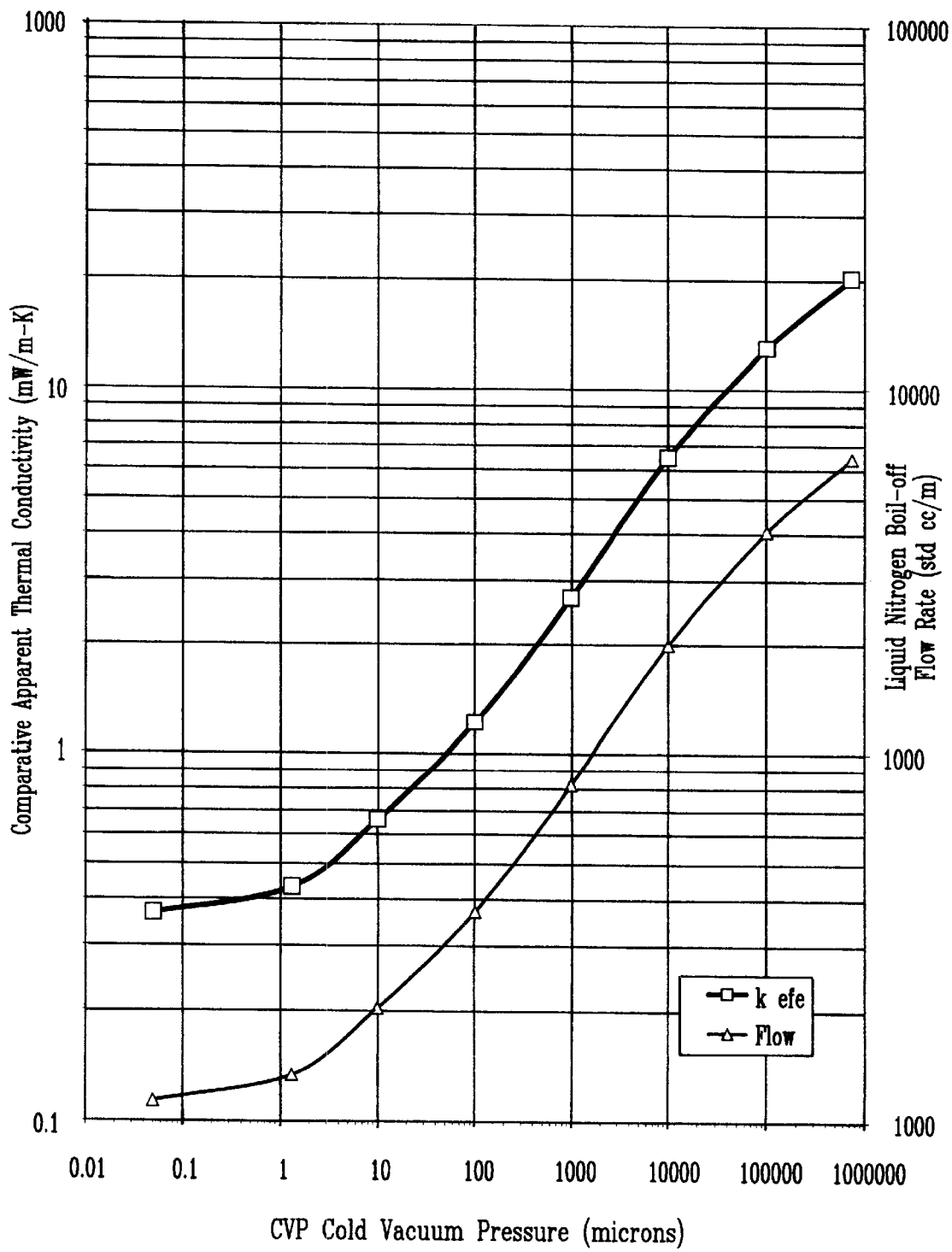
FIG. 5 is a graph showing the comparative k-value and the liquid nitrogen boil-off flow rate as a function of cold vacuum pressure for a typical series of tests.

FIG. 5 shows that the comparative apparent thermal conductivity of a given testing material has a similar relation to the boil-off flow rate. Eight test points (or vacuum levels) are shown for this example test series K122.

Figure 6:
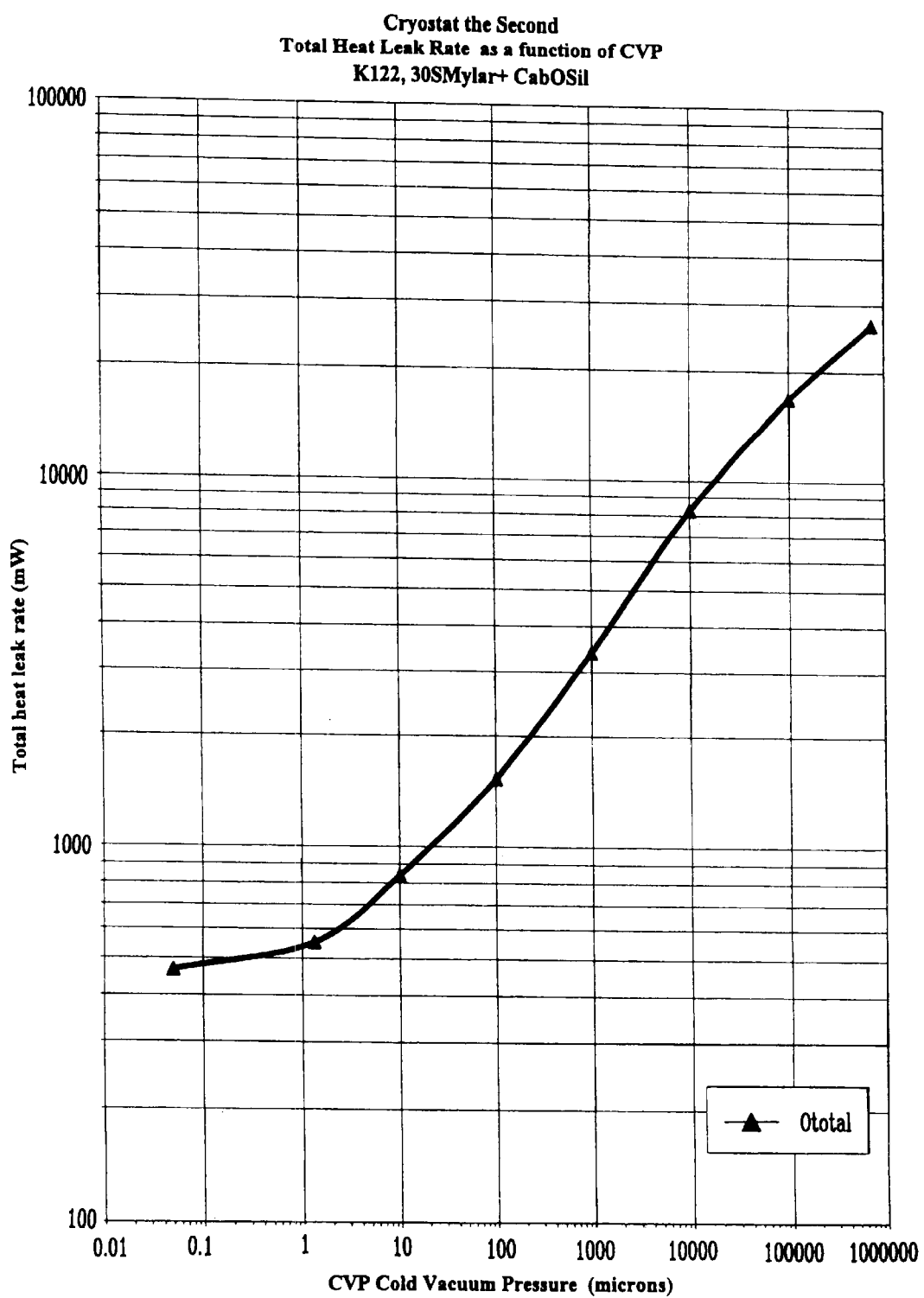
FIG. 6 is a graph showing the total heat leak rate in milliwatts into the cold mass inner vessel as a function of cold vacuum pressure for a typical series of tests.

FIG. 6 shows the total heat leak rate in milliwatts of the cryogenic boil-off device 10 for a given testing material. The total heat leak is in direct proportion to the boil-off flow rate.

Figure 7:
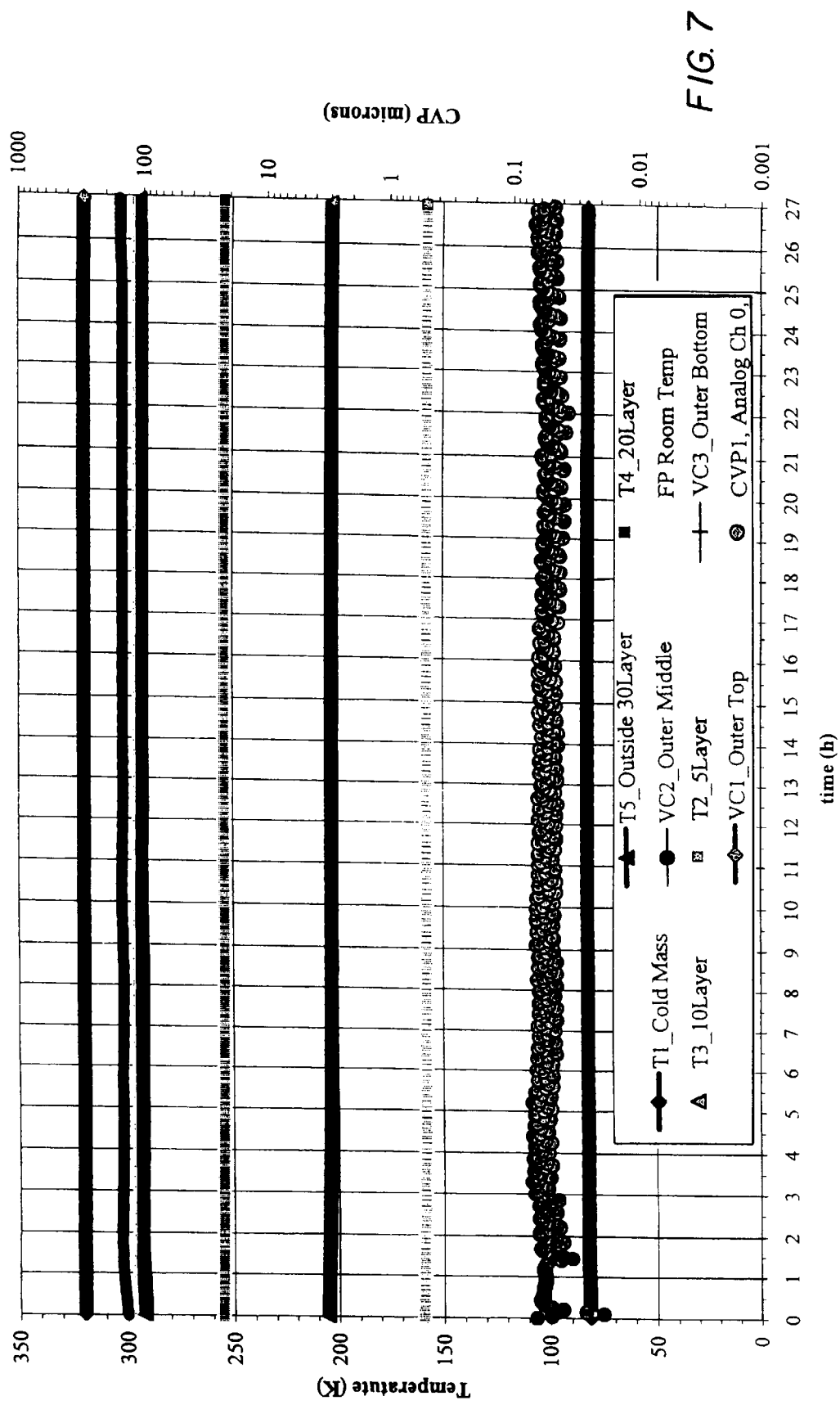
FIG. 7 is a graph showing the temperature profile across the thickness of the test material as a function of time for a typical test.

FIG. 7 shows the temperature profile versus time in hours of a plurality of temperature sensors in the testing material for a specific single test of the example test series K122. Temperature sensors were placed on the outside of the testing material 32, at various thicknesses within the testing material 32, on the inner vessel 12, and on the side of the vacuum chamber 14. The temperatures remain constant throughout the duration of the test which is critical in obtaining the desired steady-state thermal performance of the insulation test specimen.

Figure 8:
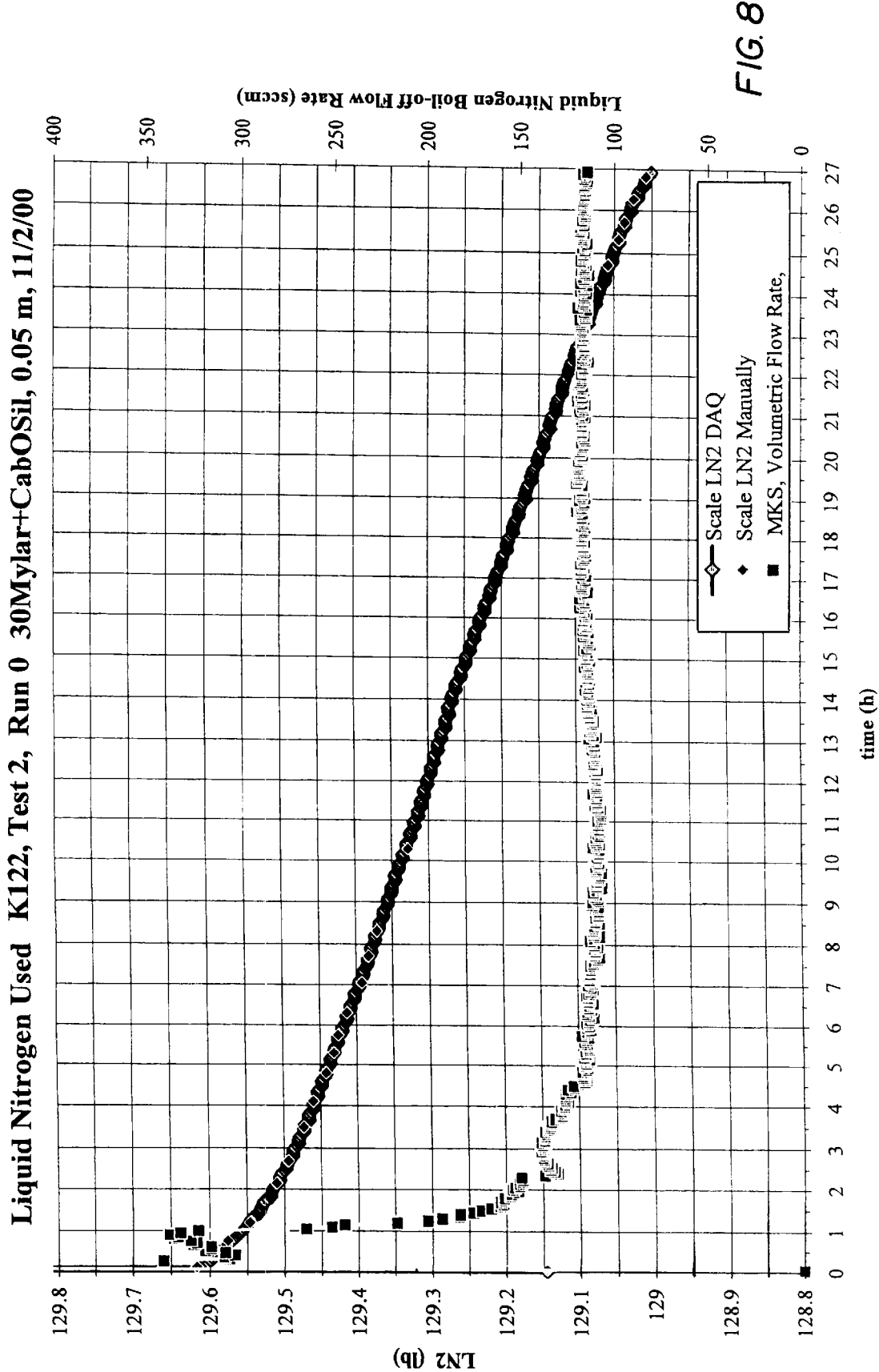
FIG. 8 is a graph showing the nitrogen boil off flow rate and the volume of liquid nitrogen in the inner vessel as a function of time for a typical test (weight in pounds and gas flow rate in standard cubic centimeters per minute).

FIG. 8 shows the nitrogen boil-off flow rate in standard cubic centimeters per minute for the same specific test. The weight in pounds of the liquid nitrogen remaining inside the cold mass versus time in hours is also shown. The flow rate is measured by a mass flow meter (or other suitable flow meter) connected by a flexible tube to the top of the cryogenic feed tube 20 and by having the entire cryogenic boil-off device 10 placed on a scale and recording the weight over time. The flowrate of the gas from the cryogenic boil-off device 10 declines sharply at the beginning of the test and levels off for the duration of the test. It is important to note that the flowrate of the boil-off gas remains stable for a sufficiently long period of time coincident with stability of the pressure and all temperatures inside the vacuum chamber.

Although the present invention has been disclosed in terms of a preferred embodiment, it will be understood that numerous additional modifications and variations could be made thereto without departing from the scope of the invention as defined by the following claims.

What is claimed is:

1. A thermal insulation apparatus adaptable for use with a boil-off flow measuring device for determining the thermal performance of a testing material, comprising:
    a) an inner vessel extending within the testing material, said inner vessel having a top, a bottom, a sidewall and a first liquid port for receiving a cryogenic fluid having a normal boiling point below ambient temperature;
    b) an outer vacuum chamber enclosing said inner vessel and the testing material and having a second liquid port;
    c) a conduit passing through said second liquid port of said outer vacuum chamber and into said first liquid port of said inner vessel through which said cryogenic fluid may pass from outside the vacuum chamber into the inner vessel;
    d) a first thermal insulation guard positioned at said top of said inner vessel;
    e) a second thermal insulation guard positioned at said bottom of said inner vessel.

2. The thermal insulation apparatus of claim 1 further comprising a device for suspending said inner vessel within said outer vacuum chamber.

3. The thermal insulation apparatus of claim 2 wherein said device for suspending said inner vessel within said outer vacuum chamber is a plurality of threads.

4. The thermal insulation apparatus of claim 3 wherein said plurality of threads are aromatic polyamide fiber threads.

5. The thermal insulation apparatus of claim 1 wherein said first thermal insulation guard and said second thermal insulation guard are comprised of material selected from the group consisting of silica aerogel, balsa wood, cork, polyurethane foam, and polystyrene foam.

6. The thermal insulation apparatus of claim 1, wherein said first thermal insulation guard and said second thermal insulation guard each comprise a plurality of discs of low thermal conductivity and a plurality of reflective film layers, disposed one each between adjacent ones of said discs.

7. The thermal insulation apparatus of claim 6, wherein said plurality of discs of low thermal conductivity are silica aerogel composite discs.

8. The thermal insulation apparatus of claim 6, wherein said plurality of reflective film layers are silvered film layers.

9. The thermal insulation apparatus of claim 1, further comprising at least one warm boundary temperature sensor located on said testing material, with said warm boundary temperature sensor being spaced a given distance from said sidewall of said inner vessel.

10. The thermal insulation apparatus of claim 9, further comprising at least one cold boundary temperature sensor located on said testing material at a location nearest said inner vessel.

11. The thermal insulation apparatus of claim 10 wherein said warm boundary temperature sensor and said cold boundary temperature sensors are thermocouples.

12. The thermal insulation test apparatus of claim 1 further comprising at least one temperature sensor feed-through port in said vacuum chamber.

13. The thermal insulation test apparatus of claim 1 further comprising at least one vacuum port in said vacuum chamber.

14. The thermal insulation test apparatus of claim 1 further comprising an end cap secured to each of said first thermal insulation guard and said second thermal insulation guard.

15. The thermal insulation apparatus of claim 1, further comprising a fitting on said bottom of said inner vessel for the attachment of a handling and wrapping tool.

16. The thermal insulation apparatus of claim 15, wherein said fitting is a double-ended connector for attaching said handling and wrapping tool to an inside and an outside of said inner vessel.

17. The thermal insulation apparatus of claim 1, wherein a fill tube having a series of holes in a lower portion outer wall extends within said conduit, permitting the combined venting and filling of said inner vessel with said cryogenic fluid passing through said fill tube.

18. The thermal insulation apparatus of claim 1, wherein an outer surface of said inner vessel sidewall is located adjacent an inner surface of said testing material.

* * * * *